(12) United States Patent
Abe et al.

(10) Patent No.: US 8,062,247 B2
(45) Date of Patent: Nov. 22, 2011

(54) TRIPLE LUMEN CATHETER

(75) Inventors: Kazuhiro Abe, Fukuroi (JP); Nobuatsu Kanie, Fukuroi (JP); Yuya Hoshinouchi, Fukuroi (JP); Toshinobu Hayakawa, Fukuroi (JP)

(73) Assignee: Covidien AG (CH)

( * ) Notice: Subject to any disclaimer, the term of this patent is extended or adjusted under 35 U.S.C. 154(b) by 0 days.

(21) Appl. No.: 11/664,306

(22) PCT Filed: Sep. 30, 2005

(86) PCT No.: PCT/EP2005/010596
§ 371 (c)(1),
(2), (4) Date: Sep. 10, 2008

(87) PCT Pub. No.: WO2006/034877
PCT Pub. Date: Apr. 6, 2006

(65) Prior Publication Data
US 2009/0024078 A1    Jan. 22, 2009

(30) Foreign Application Priority Data
Sep. 30, 2004  (JP) ................. 2004-285832

(51) Int. Cl.
*A61M 3/00*   (2006.01)
(52) U.S. Cl. ............... 604/43; 604/44; 604/45; 604/523
(58) Field of Classification Search ............ 604/43–44, 604/264, 523, 534
See application file for complete search history.

(56) References Cited

U.S. PATENT DOCUMENTS

| 4,134,402 A | | 1/1979 | Mahurkar |
| 4,894,057 A | * | 1/1990 | Howes ........................ 604/523 |
| 5,135,599 A | * | 8/1992 | Martin et al. ................ 156/294 |
| 5,395,316 A | * | 3/1995 | Martin ............................ 604/43 |
| 5,451,206 A | | 9/1995 | Young et al. |
| 5,830,196 A | | 11/1998 | Hicks |

FOREIGN PATENT DOCUMENTS

| EP | 0 386 408 A | | 9/1990 |
| EP | 0 555 780 A2 | | 8/1993 |
| EP | 555780 A2 | * | 8/1993 |
| JP | H9-276410 A | | 10/1997 |
| WO | WO 9737699 A1 | * | 10/1997 |

* cited by examiner

*Primary Examiner* — Bhisma Mehta
*Assistant Examiner* — Larry R Wilson
(74) *Attorney, Agent, or Firm* — Thomas M. Johnston, Esq.

(57) ABSTRACT

A triple lumen catheter comprises a transfusion lumen (4), a blood feeding lumen (2) and a blood removing lumen (3). The transfusion lumen (4) has a distal end and a leading end portion (12, 12A), the leading end portion progressively reducing in diameter to a proximal end. A transfusion port (4a) is formed in the proximal end of the transfusion lumen. The blood feeding lumen (2) has a blood feeding port (2a) in a region of the proximal end of the leading end portion, the blood feeding port opening at least partially in an axial direction of the leading end portion. The blood removing lumen (3) includes a pair of blood removing ports (3a, 3b) provided in opposite side walls of the catheter, the blood removing lumen extending from a distal end at least to the blood removing ports.

13 Claims, 6 Drawing Sheets

TRIPLE LUMEN CATHETER

The present invention relates to a triple lumen (multiple lumen) catheter which may be used for monitoring a hemodialysis, a temporary transfusion or a central vein pressure (hereinafter, referred to as CVP), and more particularly but not exclusively, to the structure of a triple lumen catheter in which blood is smoothly fed and removed particularly at the time of a hemodialysis.

Recently, the adoption of a triple lumen catheter has increased because of the advantage of passing transfusion fluid in addition to a general use of dialysis (for feeding and removing blood). Since a catheter must be inserted along a guide wire, most triple lumen catheters currently available adopt a so-called side-hole type where a blood feeding port or blood removing port is formed in the side portion of a catheter (for example, JP-A-2 209 159). For example, when a blood feeding port is in the form of a side hole, a large amount of retransfused blood from the blood feeding port is directed onto a blood vessel wall to apply a stimulus to the blood vessel or to generate turbulent flow, so that a thrombus easily occurs in the peripheral portion. In addition, when a blood removing port is in the form of a side hole, a catheter is influenced by a negative pressure of the blood removing lumen which acts against a blood vessel wall at the time of removing blood, so that poor blood removal frequently occurs. The problem of poor blood removal becomes obvious especially when both the blood removing port and the blood feeding port are in the form of side holes and are disposed either side of the axial direction of the catheter to face each other. In other words, when the side-hole-type blood feeding port and blood removing port are disposed to face each other, blood is directed away from the blood feeding port, perpendicular to the axial direction of the catheter. Therefore, the position of the catheter inside the blood vessel is moved in the opposite direction to the blood feeding port of the catheter, and the blood removing port, which is positioned in the side opposite to the blood feeding port, comes into contact with an inner wall of the blood vessel to occlude the vessel, so that poor blood removal occurs. As described above, the catheter is influenced by a negative pressure of the blood removing lumen, so that the blood removing port is drawn towards the blood vessel wall at the time of removing blood. Due to the synergistic interaction between a suction force of the blood removing port and an inlet pressure of the blood feeding port, the blood removing port may become occluded, so that poor blood removal easily occurs.

Subsequently, a so-called end-hole-type triple lumen catheter has been proposed, which has a blood feeding lumen which extends to a blood feeding port which opens at the leading end of a leading end portion which gradually reduces in diameter, and a blood removing lumen which extends to a pair of blood removing ports. The blood removing ports are provided in each side more rearwardly than the leading end portion to be opened in the axial direction, so as to communicate with the rear of the catheter (for example, JP-A-9 501 337).

However, there are a number of problems with catheters which are provided with the blood feeding port at the leading end of a leading end portion which gradually reduces in diameter, as follows.

(a) When the shape of the leading end portion of the catheter is configured to be sharp so that the leading end portion of the catheter is easily inserted into the human body, the blood feeding port must be reduced in size and the amount of blood that can be fed is in turn reduced, so that a blood feeding efficiency is reduced.

(b) The smaller the blood feeding port of the leading end, the more stimuli are applied to a blood vessel, because blood enters in a jet-stream shape from the blood feeding port, which is not ideal.

(c) The smaller the blood feeding port of the leading end, the higher a blood feeding pressure becomes, so that an excessive pressure is applied to a dialysis device which is connected to the rear of the catheter and an overload is applied to the dialysis device.

(d) On the other hand, when the blood feeding port of the leading end is enlarged, the shape of the leading end portion cannot be made sharp, so that insertion resistance to the catheter is increased.

(e) Since there is no lumen solely for inserting a guide wire, the blood feeding lumen must be used for insertion of the guide wire, therefore it can be more inconvenient to use such a catheter.

(f) Transfusion fluid cannot be injected (although there is a technique where transfusion fluid and blood are mixed in a blood feeding lumen to be fed into a blood vessel, it is likely that blood clots may be formed by mixing transfusion fluid and blood, which is not ideal).

The object of the present invention is therefore to provide a catheter having improved accessibility, a large blood feeding port and a large blood removing port, and to maintain a relatively sharp configuration of the leading end.

According to the present invention there is provided a triple lumen catheter comprising:

a transfusion lumen having a distal end and a leading end portion, the leading end portion progressively reducing in diameter to a proximal end, a transfusion port being formed in the proximal end of the transfusion lumen;

a blood feeding lumen having a blood feeding port in a region of the proximal end of the leading end portion, the blood feeding port opening at least partially in an axial direction of the leading end portion; and a blood removing lumen including a pair of blood removing ports provided in opposite side walls of the catheter, the blood removing lumen extending from a distal end at least to the blood removing ports.

Consequently, with the catheter according to the present invention an opening can be formed in the leading end, accessibility is excellent, and blood can be fed in a stable manner, so that poor blood supply does not occur. In addition, since the blood feeding pressure is not increased, the load on a dialysis device can be reduced and no jet stream is generated, so that an unnecessary stimulus to a blood vessel does not arise.

A partition wall may be provided between the blood feeding lumen and the blood removing lumen, such that the cross-sectional area of the blood removing lumen is greater than the cross-sectional area of the blood feeding lumen. A convex portion may protrude from an inner wall of the blood removing lumen opposite the partition wall, the transfusion lumen extending through the convex portion. The end portion may be formed with an axially extending slit and with a recess of substantially circular cross-section, the recess communicating with the slit and being adapted to engage around the convex portion.

Consequently, the transfusion lumen forming portion formed by the convex portion functions as a strengthening rib of the catheter, so that it is difficult to bend or kink the catheter, including the blood removing ports, and a stable opening can be maintained even when the blood removing ports are large. Further, with the blood removing ports being enlarged, a negative pressure can be distributed. Therefore, at the time of removing blood, the catheter approaches less closely to a blood vessel wall and the blood vessel wall is not stimulated by the catheter, so that the formation of a thrombus is suppressed.

A predetermined portion of a wall forming part of the blood feeding lumen may be set back from the leading end portion so as to form a step. The opening face of the blood feeding port may form the step.

Consequently, the cross-sectional surface of the step portion which serves as the blood feeding port is relatively sharp, and insertion resistance can be reduced. Thus, insertion into the human body can be performed easily, and the catheter can be inserted without cutting into dermal tissue.

The opening face of the blood feeding port may be inclined in the axial direction of the leading end portion towards the distal end so as to complement the shape of the leading end portion.

Since the opening surface of the blood feeding port is inclined rearwardly in the axial direction so as to follow the shape of the leading end portion, the sharp leading end shape can be maintained. Therefore, insertion resistance is reduced, insertion into the human body can be performed easily, and the catheter can be inserted without cutting into dermal tissue.

The distal end of the end portion may be tapered so as to create flow paths within the blood removing lumen to the blood removing ports.

For a better understanding of the present invention and to show more clearly how it may be carried into effect reference will now be made, by way of example, to the accompanying drawings in which.

Figure 1:
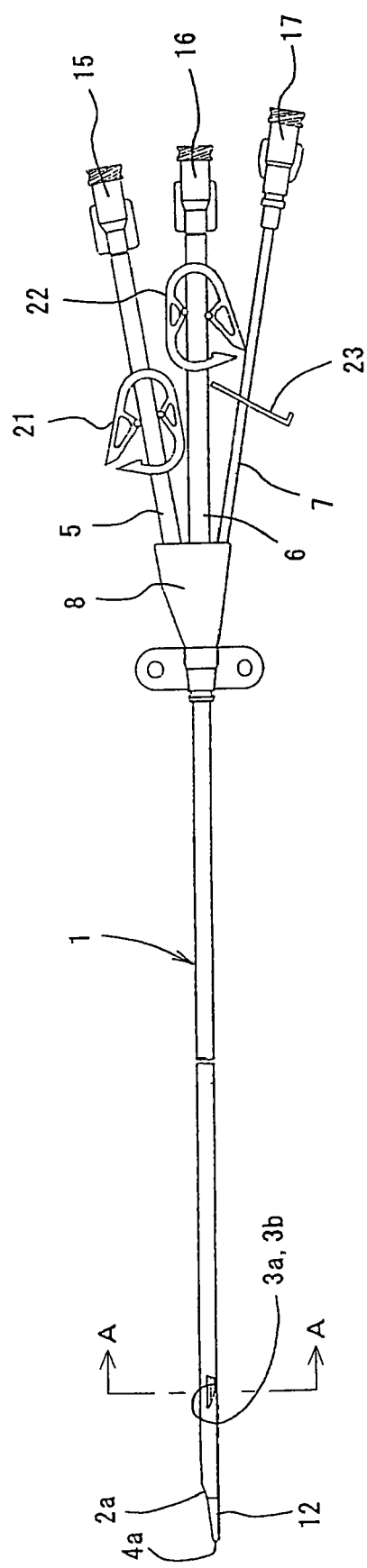
FIG. 1 is a schematic view showing the construction of a first embodiment of a triple lumen catheter according to the present invention.

FIGS. 1 to 7 show a first embodiment of a triple lumen catheter. The catheter comprises a cylindrical catheter main body 1 made of synthetic resin such as polyurethane. The main body 1 is formed with three lumens, a blood feeding lumen 2, a blood removing lumen 3, and transfusion lumen 4 which functions also as a guide-wire insertion lumen. A connection portion 8 of the catheter is provided with connection tubes 5 and 6, made of flexible synthetic resin such as silicone or polyurethane, for connection to a dialysis circuit, and a connection tube 7 integrally coupled to a base portion of the catheter main body 1 for monitoring transfusion or CVP.

Figure 2:
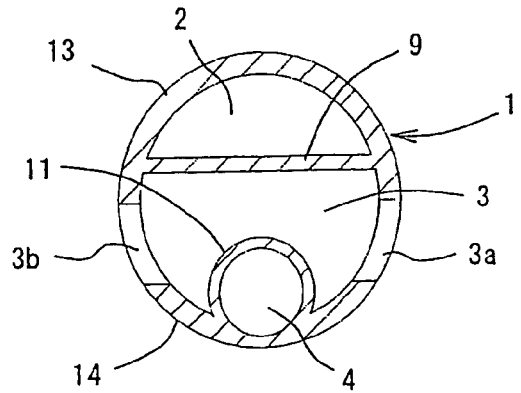
FIG. 2 is a cross-sectional view, on a larger scale, taken along the line A-A of FIG. 1.
Figure 3:
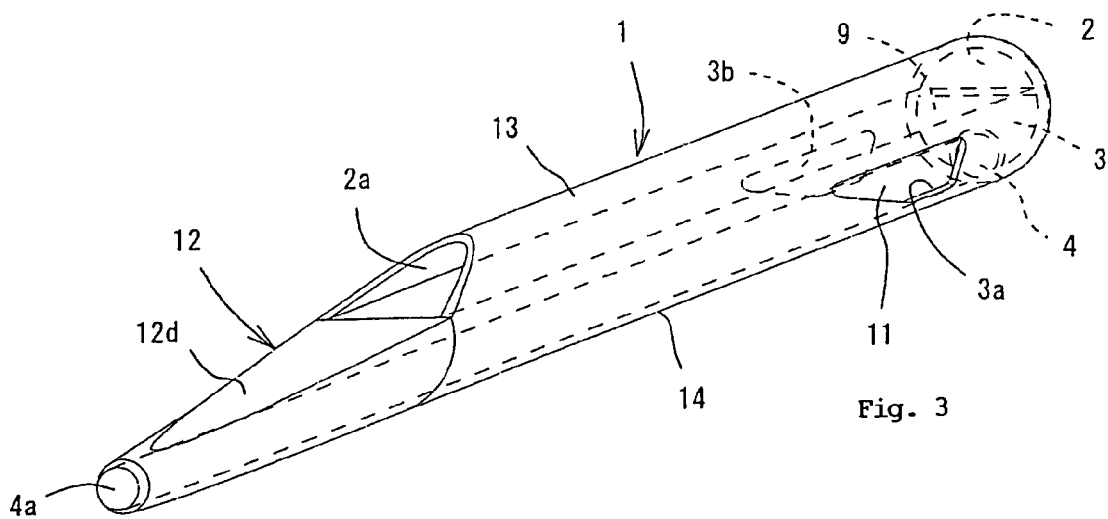
FIG. 3 is a perspective view, on a larger scale, illustrating a leading end portion of the catheter shown in FIG. 1.

More specifically, as shown in FIG. 2, the catheter main body 1 has a partition wall 9 which, in the orientation shown in FIG. 2, is at a level above the center of the body 1. The partition wall 9 forms within the main body 1 two substantially semicircular lumens having different cross-sectional areas. These are the blood feeding lumen 2 and the blood removing lumen 3, the blood removing lumen 3 having a larger cross-sectional area than the blood feeding lumen 2. Further, a convex portion 11 protrudes from the inner wall of the blood removing lumen 3 opposite the partition wall 9, to form therewithin a transfusion lumen 4 of circular cross-section. The inner diameter of the transfusion lumen 4 is substantially the same as the outer diameter of a guide wire (not shown).

Figure 5:
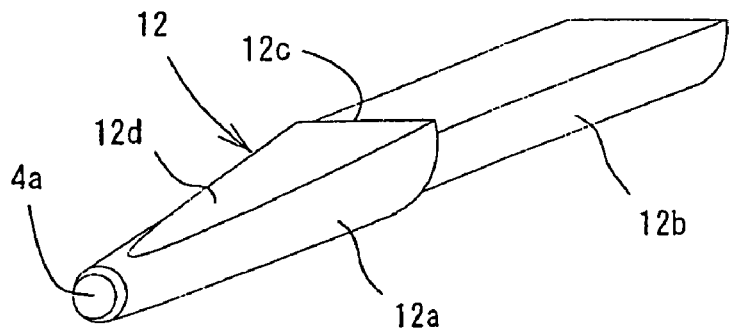
FIG. 5 is a perspective view of the catheter shown in FIG. 1 illustrating a member which is inserted to a leading end of a catheter main body so as to form a leading end portion.
Figure 6:
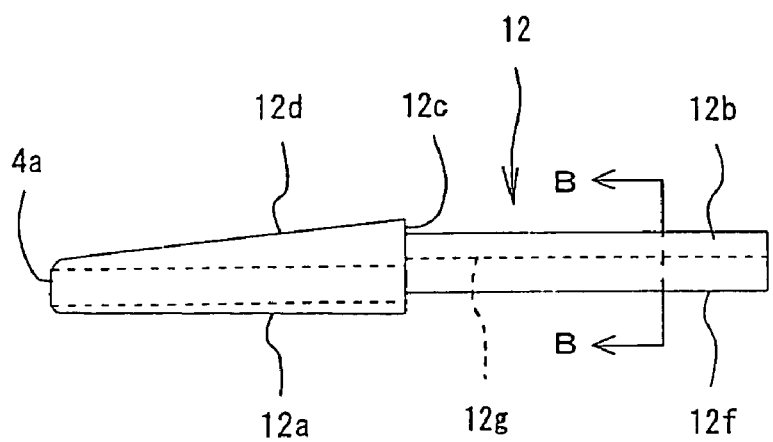
FIG. 6 is a side view of the catheter shown in FIG. 1 illustrating a leading end forming member.
Figure 7:
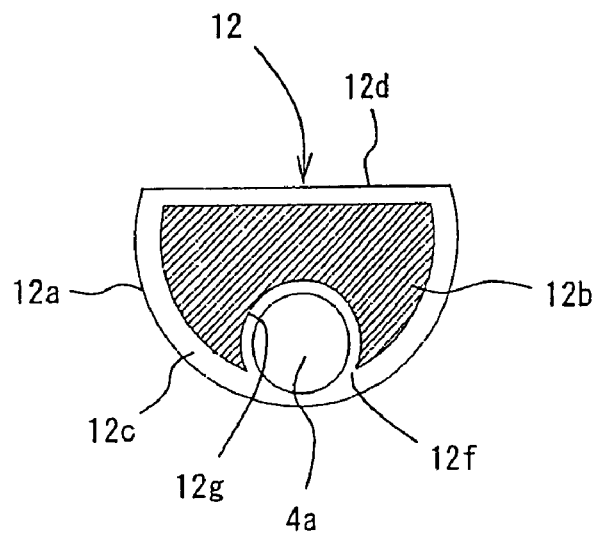
FIG. 7 is a cross-sectional view taken along line B-B of FIG. 6.
Figure 8:
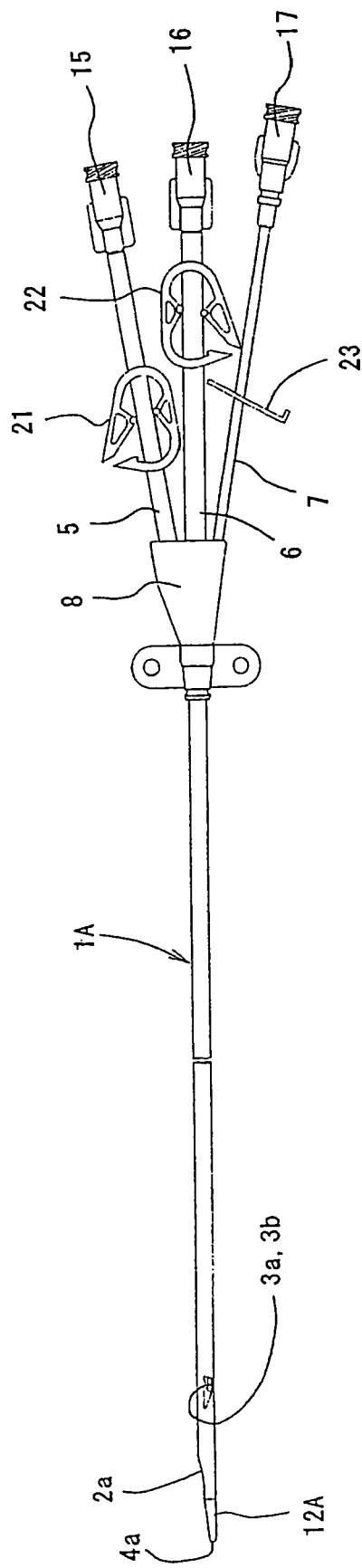
FIG. 8 is a schematic view showing the construction of a second embodiment of a triple lumen catheter according to the present invention.
Figure 9:
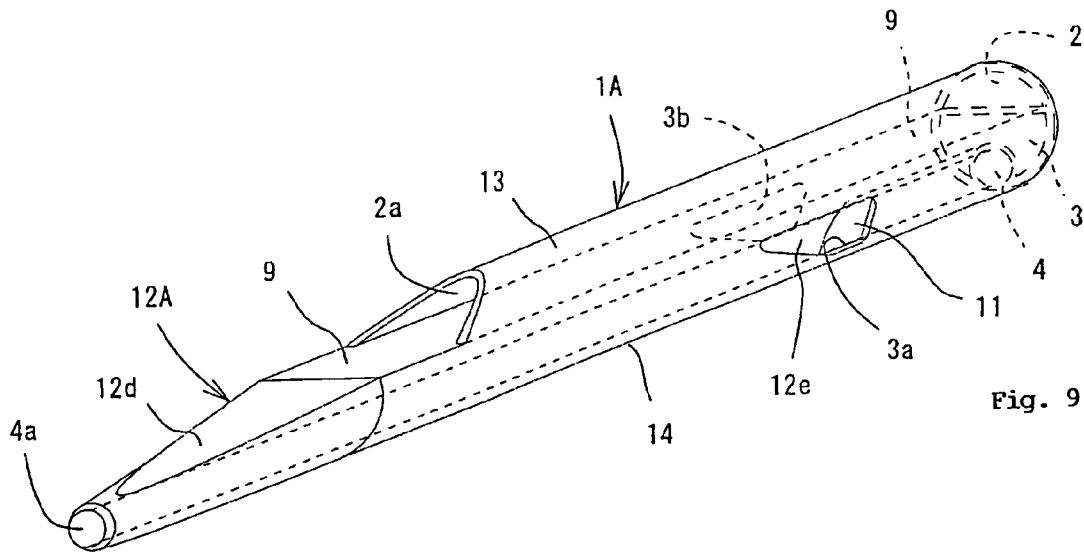
FIG. 9 is a perspective view, on a larger scale, showing a leading end portion of the catheter.
Figure 10:
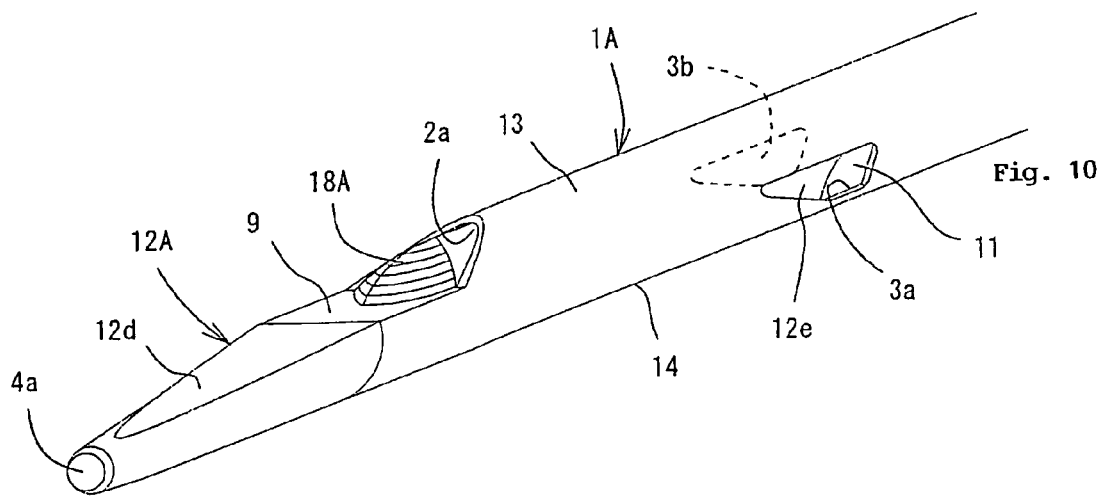
FIG. 10 is a perspective view, on a larger scale, showing the leading end portion in a state where a stiletto (core material) is inserted up to a blood feeding port inside a blood feeding lumen of the catheter.

As shown in FIGS. 5 to 7, a member 12 (hereinafter, referred to as the leading end forming member) forming the leading end portion of the catheter main body 1 is conical in a shape such that the diameter of the leading end gradually reduces. The leading end forming member 12 comprises a head portion 12a which is provided at a free end thereof with a circular transfusion port 4a communicating with the transfusion lumen 4, and a tail portion 12b which is inserted into the blood removing lumen 3 of the catheter main body 1. A step portion 12c is formed between the head portion 12a and the tail portion 12b and abuts against and is welded to the leading end surface of the catheter main body 1. A flat surface 12d is formed on the upper surface (as shown in the figures) of the head portion 12a so as to form a continuation of the partition wall 9. A slit 12f extends along the lower surface of the tail member 12b from the rear of the member 12 to a point adjacent to the step portion 12c, and a circular recess 12g is formed communicating with the slit 12f so that the convex section 11 forming the transfusion lumen 4 can be inserted into the circular recess 12g. When the tail section 12b is inserted into the blood removing lumen 3, the circular recess 12g extends around and co-operates with the convex portion 11, in a manner such that the tail portion 12b is superimposed on and bridged to the convex portion 11.

In addition, a blood feeding port 2a is formed in a blood feeding lumen forming wall portion 13 of the catheter main body 1. The blood feeding port 2a is open in the axial direction of the body 1 and communicates with the blood feeding lumen 2. The opening surface of the blood feeding port 2a is inclined rearwardly (as shown in the drawings) in the axial direction so as to follow the shape of the leading end portion 12. Formed in the wall portion 14 of the catheter main body 1 which forms the blood removing lumen, rearwardly of the blood feeding port 2a, are two blood removing ports 3a and 3b. The blood removing ports 3a and 3b are on opposite sides of the axis of the catheter shaft so as to face each other, and communicate with the blood removing lumen 3.

Lure adapters 15, 16 and 17 are integrally formed in the ends of the respective connection tubes 5, 6, and 7. Lure adapters 15 and 16 are adapted to be connected to a dialysis system at a time of dialysis, with lure adapter 15 being connected to the connection tube 5 and communicating with the blood feeding lumen 2 and lure adapter 16 being connected to the connection tube 6 and communicating with the blood removing lumen 3. The connection tube 7 is connected to the transfusion tube 4. When the lure adapters 15, 16, and 17 are not in use, closed circular caps (not shown) are attached to the opening portions of the lure adapters so that the opening portions of the lure adapters are occluded.

Figure 4:
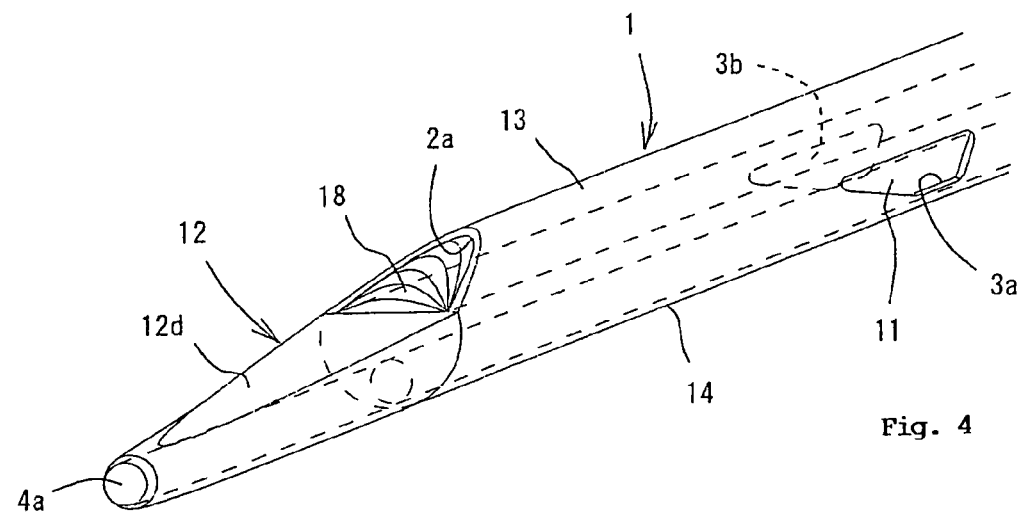
FIG. 4 is a perspective view, on a larger scale, illustrating a leading end portion of the catheter shown in FIG. 1 in a state where a stiletto (core material) is inserted up to a blood feeding port inside a blood feeding lumen of the catheter.

A shaft-shaped stiletto (core material) 18 is inserted into the blood feeding lumen 2 from the side of the base end, as in FIG. 4, when the catheter main body 1 is inserted into a blood vessel. The shaft-shaped stiletto (core material) 18 extends to the blood feeding port 2a and is made of synthetic resin material. The outer diameter of the stiletto 18 is substantially the same as or slightly smaller than the lumen diameter of the blood feeding lumen 2. Further, the shape of the leading end portion of the stiletto 18 is formed smoothly in a curved surface shape so as to match with the cross-sectional shape of the blood feeding port 2a.

Moreover, the respective connection tubes 5, 6, and 7 are provided with clamps 21, 22, and 23 (FIG. 1) occluding the respective lumens, and antithrombogenic moistening and lubricating agent (not shown) is coated at least in the region from the leading end portion 12 to the side of the base portion almost to the blood removing ports 3a and 3b in the catheter main body 1. Further, the entire catheter main body 1 may be coated with the antithrombogenic moistening and lubricating agent.

When the triple lumen catheter of the present embodiment having the above-described construction is used to perform a blood dialysis, guide wire is first placed in a vein, such as a femoral vein, an internal jugular vein, or an infraclavicular vein, the vein having abundant blood flow and a large diameter. Next, the end of the guide wire placed in a vein is inserted through the transfusion port 4a of the catheter main body 1 to be inserted into the transfusion lumen 4. Next, the catheter main body 1, into which the stiletto 18 is initially inserted up to the blooding feeding port 2a inside the blood feeding lumen 2, is pushed along the guide wire to be inserted into a vein. At this time, since the sharp leading end shape of the catheter main body 1 is maintained by the stiletto 18 of which the leading end is formed smoothly in a curved surface shape so as to match with the cross-sectional shape of the blood feeding port 2a, insertion resistance is reduced so that insertion into the human body is performed easily. For this reason, the catheter can be inserted without cutting into dermal tissue. Moreover, in the present embodiment, the opening portion of the blood feeding port 2a is formed to be inclined rearwardly in the axial direction so as to follow the shape of the leading end portion 12, as described above. In this way, insertion resistance is reduced and insertion into the human body is easily performed. Indeed, the stiletto 18 is not essential and the catheter can be used even when the stiletto 18 is not inserted into the blood feeding lumen 2. In addition, the leading end of the catheter main body 1 is in use directed in the same direction as the blood flow of the vein into which the catheter is to be placed.

Next, the guide wire is removed from the transfusion lumen 4, the stiletto 18 is removed from the blood feeding lumen 2, and the connection tube 7 which is connected to the transfusion lumen 4 is occluded by the clamp 23. Then, the lure adapter 15 connected to the connection tube 5 which communicates with the blood feeding lumen 2 is connected to the blood feeding side of the dialysis circuit and the lure adapter 16 connected to the connection tube 6 which communicates with the blood removing lumen 3 is connected to the blood removing side of the dialysis circuit to initiate blood dialysis.

When blood dialysis is initiated, blood flows into the blood removing lumen 3 from the pair of blood removing ports 3a and 3b, which are opposed to each other and communicate with the blood removing lumen 3, to be passed to the dialysis circuit. The purified blood from the dialysis circuit is passed into a blood vessel from the blood feeding port 2a, which opens in the axial direction to communicate with the blood feeding lumen 2, through the blood feeding lumen 2.

When dialysis has been completed and while the catheter main body 1 remains in the blood vessel, the lure adapter 15 of the connection tube 5 and the lure adapter 16 of the connection tube 6 are removed from the dialysis circuit, and the blood feeding lumen 2 and the blood removing lumen 3 are flushed with heparin lock isotonic sodium chloride solution. Further, closed circular caps (not shown) are attached to the opening portions of the respective lure adapters 15 and 16 so as to occlude the opening portions of the respective lure adapters 15 and 16.

As such, in the triple lumen catheter of the present embodiment, the transfusion lumen 4 extends up to the transfusion port 4a which opens at the leading end of the leading end portion 12 which gradually reduces in diameter, and the blood feeding lumen extends up to the blood feeding port 2a which opens in the axial direction near the leading end so that, during hemodialysis, blood is fed by the blood feeding port 2a which opens in the axial direction. Therefore, the leading end member can have an aperture at the end thereof, accessibility is excellent, and blood can be fed in a stable manner, so that poor blood feeding is avoided. In addition, since blood feeding pressure is not increased, the load on a dialysis device can be reduced and no jet stream is generated, so that an unnecessary stimulus to a blood vessel is avoided.

In addition, the partition wall 9 is provided between the blood feeding lumen 2 and the blood removing lumen 3 in such a way that the cross-sectional area of the blood removing lumen is larger than that of the blood feeding lumen. Further, the convex portion 11 is formed in the position of an inner wall of the blood removing lumen 3 opposite to the partition wall so as to extend towards one side of the partition wall 9, and the convex portion 11 is provided with the transfusion lumen 4. Therefore, the transfusion lumen forming portion composed of the convex portion 11 functions as a strengthening rib of the catheter main body 1, so that it is difficult to bend or kink the catheter, including the blood removing ports 3a and 3b, and a stable opening can be maintained even when the blood removing ports 3a and 3b are enlarged. Further, with the blood removing ports 3a and 3b being enlarged, a negative pressure can be distributed. Therefore, at the time of removing blood, the catheter main body 1 approaches less closely to the wall of the blood vessel wall and the blood vessel wall is not stimulated by the catheter, so that a thrombus can be prevented from being formed.

In addition, since the opening surface of the blood feeding port 2a is inclined rearwardly in the axial direction so as to follow the shape of the leading end 12, the sharp leading end shape can be maintained. Therefore, insertion resistance can be reduced and the insertion into the human body is easily performed, so that the catheter can be inserted without cutting into dermal tissue.

The catheter-insertion resistance is further reduced by the antithrombogenic moistening and lubricating agent which is coated at least in the region from the leading end portion 12 to the side of the base portion almost to the blood removing ports 3a and 3b in the catheter main body 1, so that a smooth insertion can be accomplished. Further, a thrombus can be prevented from being formed in the blood removing ports 3a and 3b, and the catheter can be kept open for a long time.

FIGS. 8 to 12 show a second embodiment of a triple lumen catheter. In the drawings of FIGS. 8 to 12 like reference numerals are used to identify the same components as those of the above-described first embodiment, and the descriptions thereof are omitted.

In the triple lumen catheter of the present embodiment, a predetermined portion of a blood-feeding-lumen forming wall portion 13 excluding the partition wall 9 is notched (set back) at a distance from the leading end so as to form a step portion, and the opening surface of the blood feeding port 2a, which is the cross-sectional surface of the step portion, is inclined rearwardly in the axial direction. Further, when a catheter main body 1A is inserted into a blood vessel, a shaft-shaped stiletto (core material) 18A, which extends up to a blood feeding port 2a and is made of synthetic resin material, is inserted into the blood feeding lumen 2 from the end of the catheter as in FIG. 10.

Figure 11:
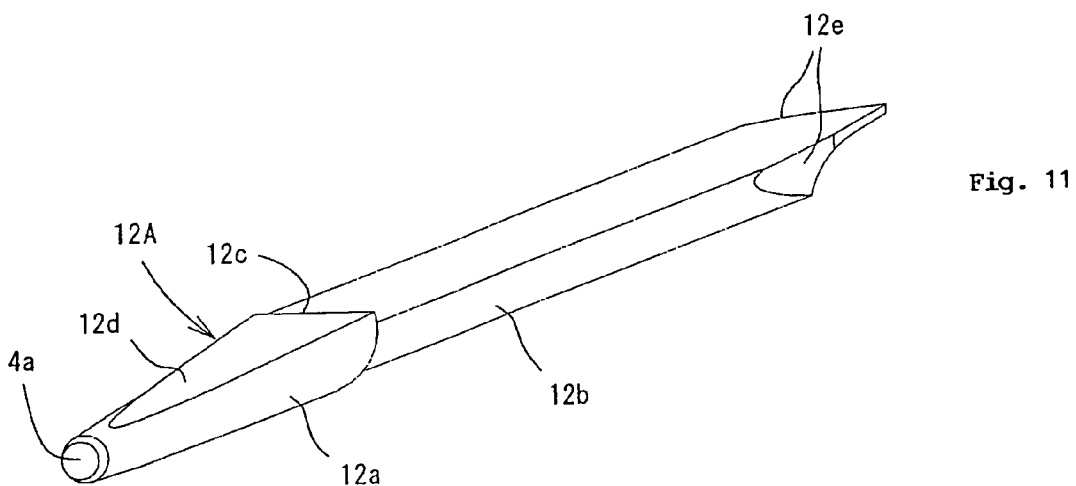
FIG. 11 is a perspective view showing a leading end forming member which is inserted to a leading end of a catheter main body so as to form the leading end portion.
Figure 12:
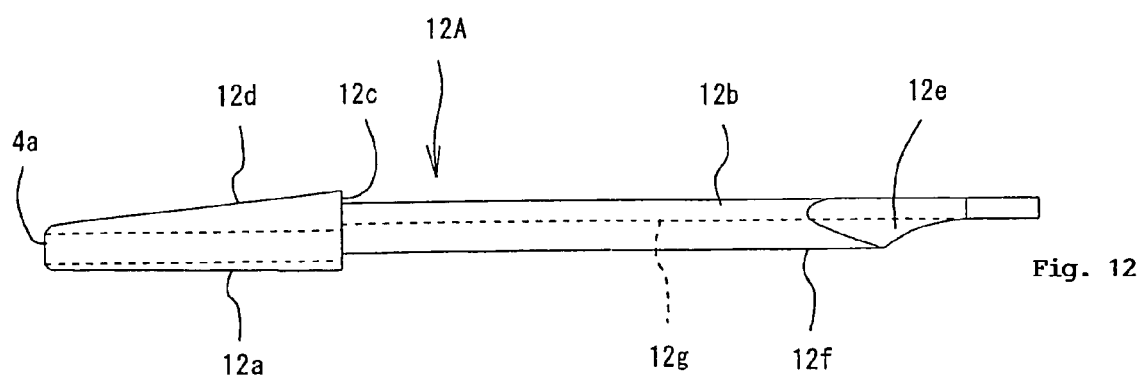
FIG. 12 is a side view showing a leading end forming member of the catheter.

As shown in FIGS. 11 and 12, a member 12A (hereinafter, referred to as the leading end forming member) forming the leading end portion of the catheter main body 1A is conical in shape such that the diameter of the leading end gradually reduces. The leading end forming member 12A comprises a head portion 12a which is provided at a free end thereof with a circular transfusion port 4a communicating with the transfusion lumen 4, and a long tail portion 12b which is inserted into the blood removing lumen 3 of the catheter main body 1A so as to extend up to blood removing ports 3a and 3b. A step portion 12c is formed between the head portion 12a and the tail portion 12b and abuts against and is welded to the leading end surface of the catheter main body 1A. A flat surface 12d is formed on the upper surface of the head portion 12a so as to form a continuation of the partition wall 9. A flow path determining portion 12e at the end of the member 12A opposite the port 4a is formed in a tapered shape, the width of the portion 12e narrows towards the rear of the member 12A. Both side surfaces of the rear region of the tail portion 12b are tapered so as to form flow paths inside the blood removing ports 3a and 3b. A slit 12f extends along the lower surface of the tail member 12b from the rear of the member 12A to a point adjacent to the step portion 12c, and a circular recess 12g is formed communicating with the slit 12f so that the convex section 11 forming the transfusion lumen 4 can be inserted into the circular recess 12g. When the tail member 12b is inserted into the blood removing lumen 3, the circular recess extends around and co-operates with the convex portion 11 in a manner such that the tail member 12b is superimposed on and bridged to the convex portion 11.

In addition, even in the present embodiment, antithrombogenic moistening and lubricating agent (not shown) is coated at least in the region from the leading end portion to the side of the base portion almost to the blood removing ports 3a and 3b in the catheter main body 1A. Further, the entire catheter main body 1A may be coated with the antithrombogenic moistening and lubricating agent. Components other than those above are the same as those of the first embodiment, and the present embodiment has all the functions of the first embodiment.

Accordingly, the triple lumen catheter of the present embodiment also has the same effect as the above-described embodiment. In other words, the leading end shape can have an aperture at the end thereof, accessibility is excellent, and blood can be fed in a stable manner, so that poor blood feeding can be avoided. In addition, since the blood feeding pressure is not increased, the load on a dialysis device can be reduced and no jet stream is generated, so that an unnecessary stimulus to a blood vessel is avoided.

In addition to a strengthening rib effect due to the presence of the convex portion 11 forming the transfusion lumen 4, the leading end to the blood removing ports 3a and 3b of the catheter main body 1A are further supported from the inside by the long tail portion 12b of the leading end forming member 12A. Therefore, the entire catheter including the blood removing ports 3a and 3b is even more resistant to kinking or bending, and a stable opening can be maintained even when the blood removing ports 3a and 3b are enlarged. Further, with the blood removing ports 3a and 3b being enlarged, a negative pressure can be distributed. Therefore, at the time of removing blood, the catheter main body 1 approaches less closely to a blood vessel wall, and the blood vessel wall is not stimulated by the catheter, so that a thrombus can be prevented from being formed.

In addition, since the opening surface of the blood feeding port 2a is inclined rearwardly in the axial direction, the sharp leading end shape can be maintained. For this reason, insertion resistance can be reduced and insertion into the human body is easily performed, so that the catheter can be inserted without cutting into dermal tissue.

The catheter insertion resistance is further reduced by the antithrombogenic moistening and lubricating agent which is coated at least in the region from the leading end portion to the side of the base portion close to the blood removing ports 3a and 3b in the catheter main body 1, so that a smooth insertion can be accomplished. Further, a thrombus can be prevented from being formed into the blood removing ports 3a and 3b, and the catheter can be kept open for a long time.

The invention claimed is:

1. A triple lumen catheter, which comprises:
a catheter body defining a longitudinal axis and having a proximal trailing end and a distal leading end, the catheter body having an internal partition wall forming a blood feeding lumen and a blood removal lumen, and an internal arcuate wall defining a transfusion lumen protruding from an inner wall of the blood removal lumen, the internal arcuate wall being spaced from the internal partition wall, the catheter body having a blood feeding port at the leading end in fluid communication with the blood feeding lumen and a blood removal port proximal of the leading end in fluid communication with the blood removal lumen, the catheter body including an oblique surface adjacent the leading end, the oblique surface at least partially defining the blood feeding port; and
a leading member mounted to the leading end of the catheter body and including a tail portion positionable within the blood removal lumen such that the blood feeding port is unobstructed by the leading member, the leading member having a transfusion channel in fluid communication with the transfusion lumen of the catheter body and terminating in a transfusion port remote from the catheter body, the leading member defining a cross-section transverse to the longitudinal axis reducing in dimension towards the transfusion port.

2. The triple lumen catheter according to claim 1 wherein the oblique surface is spaced from the leading end to define a stepped region.

3. The triple lumen catheter according to claim 1 wherein the catheter body has first and second blood removal ports in fluid communication with the blood removal lumen.

4. The triple lumen catheter according to claim 3 wherein the first and second blood removal ports are in general diametrical opposed relation.

5. The triple lumen catheter according to claim 1 wherein the blood removal lumen defines a cross-sectional area greater than a cross-sectional area of the blood feeding lumen.

6. The triple lumen catheter according to claim 1 wherein the leading member defines a substantially planar surface in oblique relation relative to the longitudinal axis and in general alignment with the oblique surface of the catheter body to reduce a cross-sectional profile of the leading member.

7. The triple lumen catheter according to claim 1 wherein the tail portion of the leading member includes an arcuate flow path surface adjacent the blood removal port of the catheter body to facilitate flow of blood through the blood removal port.

8. The triple lumen catheter according to claim 1 wherein the internal arcuate wall is substantially annular in cross-section to define a generally annular shape to the transfusion lumen.

9. The triple lumen catheter according to claim 1 wherein the internal wall is substantially circular in cross-section to define a generally circular-shape to the transfusion lumen.

10. A triple lumen catheter, which comprises:

a catheter body defining a longitudinal axis and having proximal and distal ends, the catheter body having an internal partition wall forming a blood feeding lumen and a blood removal lumen, and an internal arcuate wall defining a third lumen wholly disposed within the blood removal lumen, the catheter body having a blood feeding port at the distal end of the catheter body in fluid communication with the blood feeding lumen and a blood removal port proximal of the blood feeding port in fluid communication with the blood removal lumen, the blood feeding port of the catheter body terminating in an outer oblique surface, the oblique surface at least partially defining the blood feeding port and forming an axially directed opening face, and further having a leading end portion adjacent the distal end and including a tail portion positionable within the blood removal lumen such that the leading end portion does not occlude the blood feeding port, the leading end portion defining a third axial port in fluid communication with the third lumen and being distal of the blood feeding port and the blood removal port, the leading end portion defining a cross-sectional dimension transverse to the longitudinal axis decreasing toward the third axial port.

11. The triple lumen catheter according to claim 10 wherein the internal partition wall of the catheter body is substantially linear to define first and second generally semi-hemispherical lumens, the first and second lumens corresponding to the blood feeding lumen and the blood removal lumen, respectively.

12. The triple lumen catheter according to claim 10 wherein the internal arcuate wall is substantially annular in cross-section to define an annular-shaped lumen.

13. The triple lumen catheter according to claim 10 wherein the catheter body includes first and second opposed blood removal ports.

* * * * *